US010943280B2

(12) United States Patent
King (10) Patent No.: US 10,943,280 B2
(45) Date of Patent: Mar. 9, 2021

(54) CUSTOM ORTHOTIC PILLOW SYSTEM (71) Applicant: Shawn Anthony King, Alberta (CA)

(72) Inventor: Shawn Anthony King, Alberta (CA)

(*) Notice: Subject to any disclaimer, the term of this patent is extended or adjusted under 35 U.S.C. 154(b) by 231 days.

(21) Appl. No.: 15/945,702

(22) Filed: Apr. 4, 2018

(65) Prior Publication Data
US 2019/0307269 A1 Oct. 10, 2019

(51) Int. Cl.
G06Q 30/06 (2012.01)
A47G 9/10 (2006.01)
A61B 5/00 (2006.01)
A61B 5/107 (2006.01)
B33Y 80/00 (2015.01)

(52) U.S. Cl.
CPC .......... G06Q 30/0621 (2013.01); A47G 9/10 (2013.01); A47G 9/109 (2013.01); A47G 9/1081 (2013.01); A61B 5/0064 (2013.01); A61B 5/107 (2013.01); B33Y 80/00 (2014.12)

(58) Field of Classification Search
None
See application file for complete search history.

(56) References Cited

U.S. PATENT DOCUMENTS

| 6,751,496 | B2* | 6/2004 | Su | G01R 33/3415 |
| | | | | 324/318 |
| 6,957,497 | B2* | 10/2005 | Greenawalt | A61B 5/1072 |
| | | | | 33/512 |
| 6,993,800 | B2* | 2/2006 | Greenawalt | A47G 9/10 |
| | | | | 5/636 |
| 8,528,138 | B2* | 9/2013 | Hooper | A47G 9/10 |
| | | | | 5/636 |
| 9,888,906 | B2* | 2/2018 | Toji | A61B 8/08 |
| 10,357,955 | B2* | 7/2019 | Ziolek | B29C 64/171 |
| 2002/0013526 | A1* | 1/2002 | Su | G01R 33/3415 |
| | | | | 600/422 |
| 2005/0061332 | A1 | 3/2005 | Greenawalt | |
| 2005/0150051 | A1* | 7/2005 | Greenawalt | A47G 9/10 |
| | | | | 5/636 |
| 2005/0150124 | A1* | 7/2005 | Greenawalt | A61B 5/1072 |
| | | | | 33/512 |
| 2010/0332009 | A1* | 12/2010 | Hooper | A47G 9/10 |
| | | | | 700/103 |

(Continued)

FOREIGN PATENT DOCUMENTS

JP 6621104 B1 * 12/2019 ............. B33Y 80/00

OTHER PUBLICATIONS

Xu, W., et al., "Building Customized Cushion Seats Using Stereo Vision for the Disabled," 2010 Seventh International Conference on Information Technology: New Generations, pp. 275-281, Apr. 1, 2010. (Year: 2010).*

(Continued)

Primary Examiner — Nicholas D Rosen
(74) Attorney, Agent, or Firm — Argus Intellectual Enterprise; Daniel Enea; Jordan Sworen (57) ABSTRACT A system includes a scanner-device, and a computer-device communicably-coupled to the scanner-device. The scanner-device is configured to scan a neck, head and shoulder of a user. The system is useful for providing a custom orthotic pillow based on the scan and individual measurements of the user. In this way a customized comfortable pillow can be achieved.

14 Claims, 6 Drawing Sheets (56) References Cited

U.S. PATENT DOCUMENTS

2015/0164479 A1\* 6/2015 Toji ................... A61B 8/5207
                                                        600/440
2016/0349738 A1\* 12/2016 Sisk ................... B29C 64/393
2017/0305093 A1\* 10/2017 Ziolek ................. B29C 64/106

OTHER PUBLICATIONS

Machine translation of Sato, Japanese Patent 6,621,104 B1, machine translation produced Apr. 15, 2020. (Year: 2020).\*

\* cited by examiner

CUSTOM ORTHOTIC PILLOW SYSTEM

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

1. FIELD OF THE INVENTION

The present invention relates generally to the field of orthotic pillows and more specifically relates to a system for providing a custom orthotic pillow.

2. DESCRIPTION OF RELATED ART

Pillows have existed for centuries. Typically, a pillow consists of an envelope filled with a soft material, such as down, spun fibres, foam rubber, and the like. While these pillows provide comfort during sleep they also orient the head of person so as to misalign the head with the spine. This misalignment may result in physical problems to the human body. Recently, pillows have been designed having a top surface contoured in a manner to attempt to better align the head and spine during sleep. These pillows however are typically designed with a top surface having one fixed shape. As such, these pillows do not properly conform to all users having different neck lengths, head sizes or other physical differences between individuals. Thus, a suitable solution is desired.

U.S. Pub. No. 2005/0061332 to Kent Greenawalt relates to a method and apparatus for scanning feet for the purpose of manufacturing orthotics and other footwear. The described method and apparatus for scanning feet for the purpose of manufacturing orthotics and other footwear includes a single or dual flatbed scanner and a computer, all the data required to construct a corrective device may be obtained from a scan or scans of the foot. Observed features and color variations, as well as physical measurements are used to overcome imperfections of a patient's foot.

BRIEF SUMMARY OF THE INVENTION

In view of the foregoing disadvantages inherent in the known orthotic pillow art, the present disclosure provides a novel custom orthotic pillow system. The general purpose of the present disclosure, which will be described subsequently in greater detail, is to provide a system for scanning a neck and head of a user to provide a custom orthotic pillow.

A system is disclosed herein. The system includes a scanner-device which may include an image-capture means, a measurement-means and a communication-means. The image-capture means may be configured to capture at least one image of at least one body-part of a user, and the measurement-means may be configured to provide at least one measurement of the at least one body-part of the user.

Further, a computer-device may be communicably-coupled to the scanner-device. The computer-device may include a processor and a memory—the processor may be configured to receive the at least one image of the at least one body-part of the user and the at least one measurement of the at least one body-part of the user via the communication-means. In addition to this, the processor may be configured to generate at least one pillow-profile based on the at least one image and the at least one measurement. The memory may be configured to then store the at least one image, the at least one measurement and the at least one pillow-profile.

A method of using system is also disclosed herein. The method of using system may comprise the steps of: providing the system as above; using the image-capture means to capture the at least one image of the at least one body-part of the user; using the measurement-means to provide the at least one measurement of the at least one body-part of the user; reviewing the at least one pillow-profile of the user based on the at least one image and the at least one measurement; and creating the custom-pillow based on the pillow-profile.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a custom orthotic pillow system, constructed and operative according to the teachings of the present disclosure.

The various embodiments of the present invention will hereinafter be described in conjunction with the appended drawings, wherein like designations denote like elements.

DETAILED DESCRIPTION

As discussed above, embodiments of the present disclosure relate to an orthotic pillow and more particularly to a custom orthotic pillow system as used to provide a means for creating a custom orthotic pillow.

Generally, disclosed is a system including a scanner. The scanner may be configured to scan the neck of the user in three positions: supine, right-side and left-side. Further, the scanner may measure a circumference of the neck, the head and a length between a shoulder of the user and the neck/ head. Based off of the measurements, a pillow may be built custom for the user to provide support and promote a neutral spine. The scanner may provide an accurate analysis and measurement of the head and neck to provide the pillow with the best support possible in order to prevent issues such as neck pain, upper back pain, headaches, etc. and promote a better night's sleep.

Referring now more specifically to the drawings by numerals of reference, there is shown in FIGS. 1-5, various views of a system 100.

Figure 1:
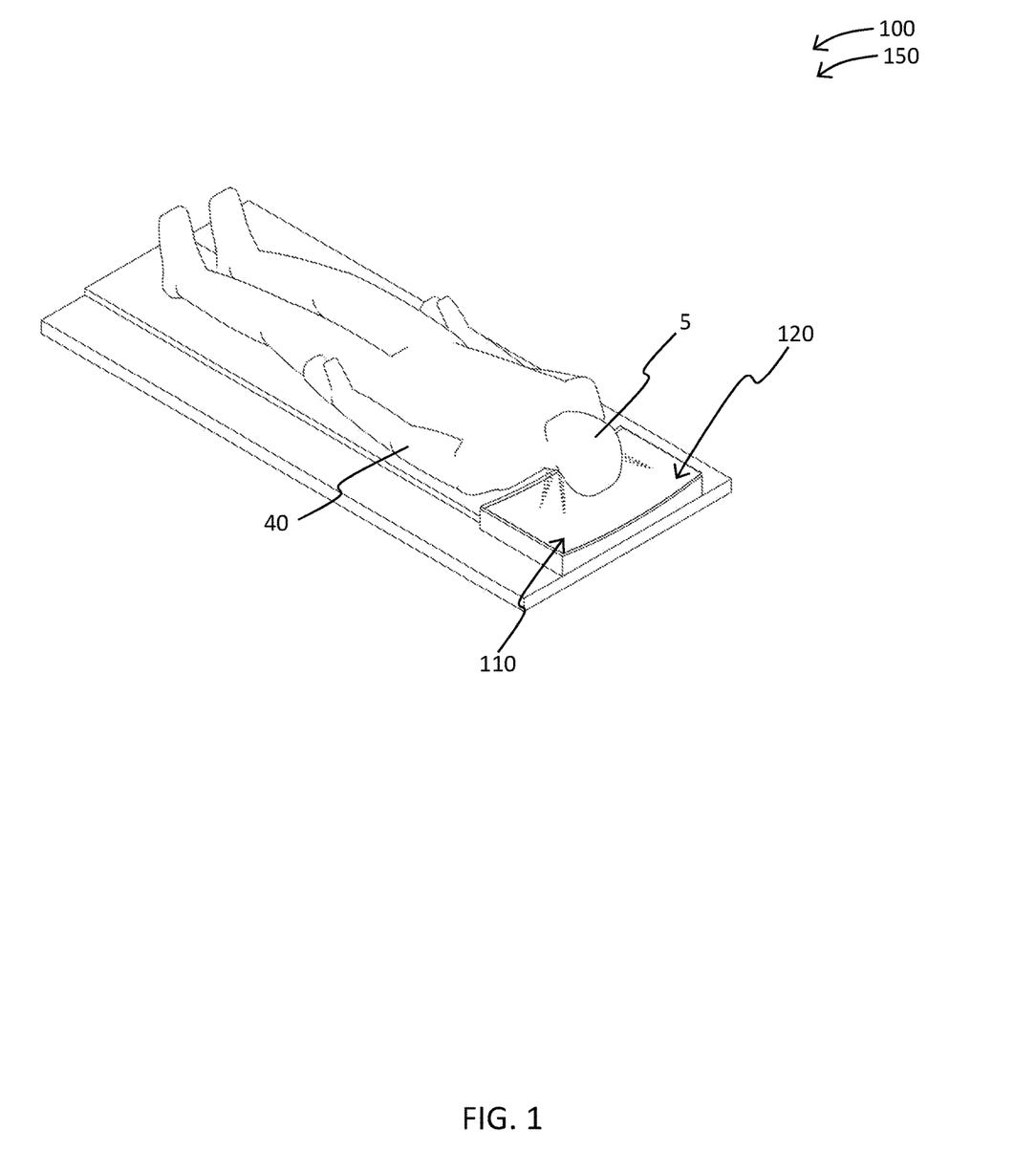
FIG. 1 is a front perspective view of the system during an 'in-use' condition, according to an embodiment of the disclosure.

FIG. 1 shows a system 100 during an 'in-use' condition 150, according to an embodiment of the present disclosure. As illustrated, the system 100 may include a scanner-device 110 and a computer-device 120. As shown, the system 100 may be used for scanning a neck of a user 40 to provide a custom orthotic pillow.

Figure 2:
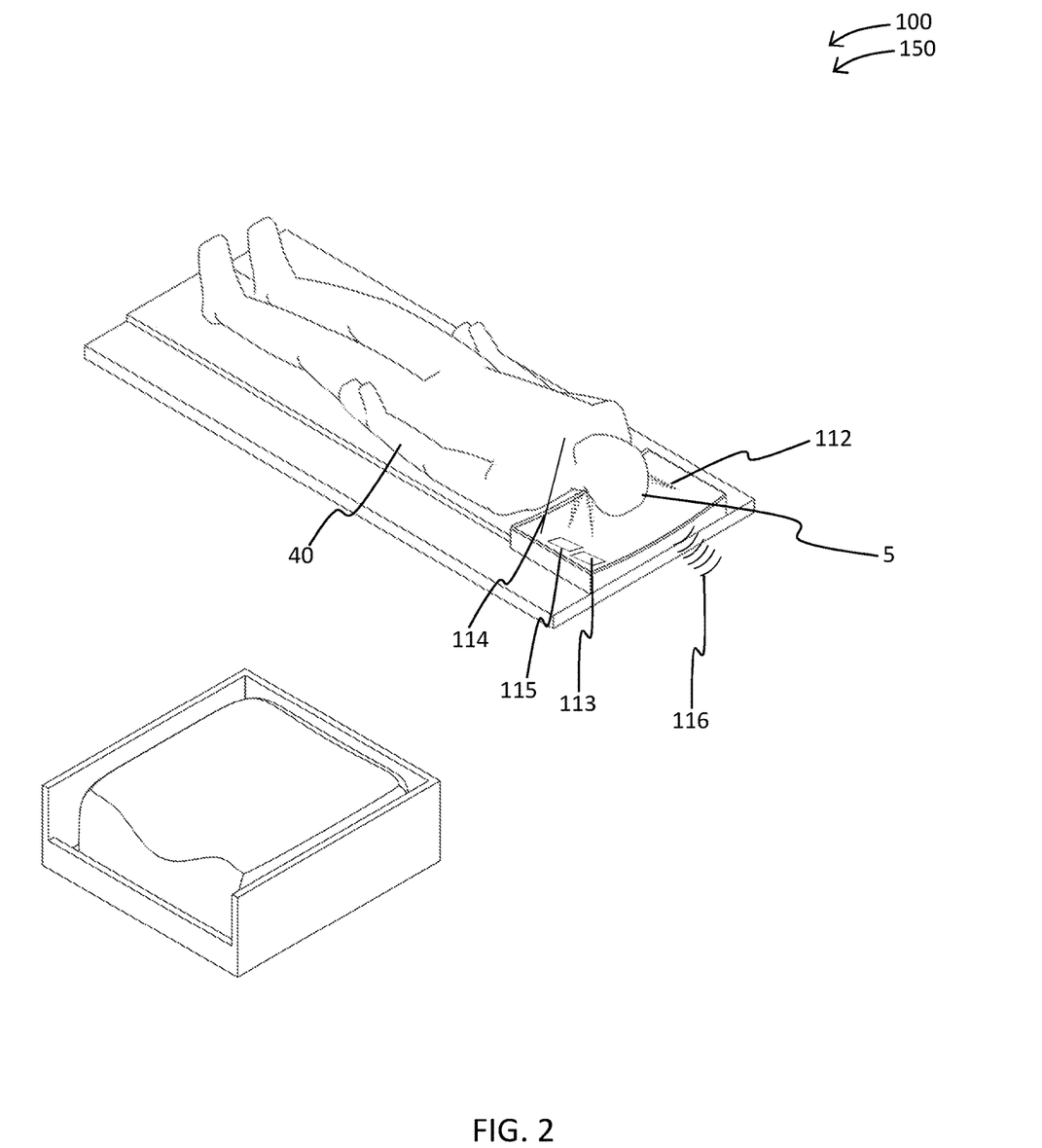
FIG. 2 is a front perspective view of the system of FIG. 1, according to an embodiment of the present disclosure.

Referring now to FIG. 2 showing a front perspective view of the system 100 of FIG. 1, according to an embodiment of the present disclosure. The scanner-device 110 may include an image-capture means 112, a measurement-means 114 and a communication-means 116. The image-capture means 112 may be configured to capture at least one image 113 of at least one body-part 5 of a user 40. In a preferred embodiment, the image-capture means 112 may include at least one imaging laser-beam. A laser rangefinder may also be provided and combined with controlled steering of the at least one imaging laser-beam, the at least one image 113 may be created.

It should be appreciated that other image-capture means 112 may be used. For example, magnetic resonance imaging, x-ray beams, soundwaves, and the like. In the preferred embodiment, the at least one image 113 may include three images 113 and the at least one body-part 5 may be a neck of the user 40. In this embodiment, the three images 113 may be a supine-position of the neck, a right-side position of the neck, and a left-side position of the neck. In this embodiment, an operator of the system 100 may use the scanner-device 110 to scan the supine-position, the right-side position and the left-side position to generate a full three-dimensional rendering of the user's 40 neck.

The measurement-means 114 may be configured to provide at least one measurement 115 of the at least one body-part 5 of the user 40. In the preferred embodiment, the measurement-means 114 includes at least one measurement laser-beam. The at least one measurement laser-beam may be a pulse of laser light and a time it takes for the pulse of laser light to reach a measure-target may be calculated to determine the at least one measurement 115.

The at least one body-part 5 may further include a head and a shoulder of the user 40. In this embodiment, the at least one-measurement 115 may include a circumference-measurement of the head and the neck. Further, the at least one-measurement 115 may include a length-measurement from the shoulder to the head. In this embodiment, the operator of the system 100 may use the scanner-device 110 to measure the circumference of the head and the neck, and also to measure the length from the shoulder to the head and neck of the user 40. In one embodiment, the system 100 may further include a reference-means configured to provide a reference point for the image-capture means 112 and the measurement-means 114.

Other analysis and evaluation means may be used along with the scanner-device 110, or in some embodiments, in place of the scanner-device 110. Such other means may include the use of foam casts. In this embodiment, a foam casting-device may be made from a crushable foam-material and the neck, head and shoulder of the user 40 may imprinted into the foam-casting device to create a foam-cast. As above, this foam-cast may be used along with the scanner-device 110 to provide an in-depth analysis and evaluation of the measurements of the neck, head and shoulder of the user 40. In other embodiments, the foam-cast may be utilized without the scanner-device 110. In one embodiment, the measurements of the foam-cast may be inputted into the computer-device 120. In other embodiments, the custom-pillow may be created solely from the foam-cast without inputting data into the computer-device 120. It should also be appreciated that other imaging, measurement, evaluation and analysis means may be used to create the custom-pillow.

The communication-means 116 may be wireless (as shown in this figure) or may be non-wireless coupling the scanner-device 110 and the computer-device 120. In this embodiment, the communication-means 116 may be WIFI, BLUETOOTH®, Infrared (IR), and the like. However, it should be appreciated that other communication-means 116 may be used.

Figure 3:
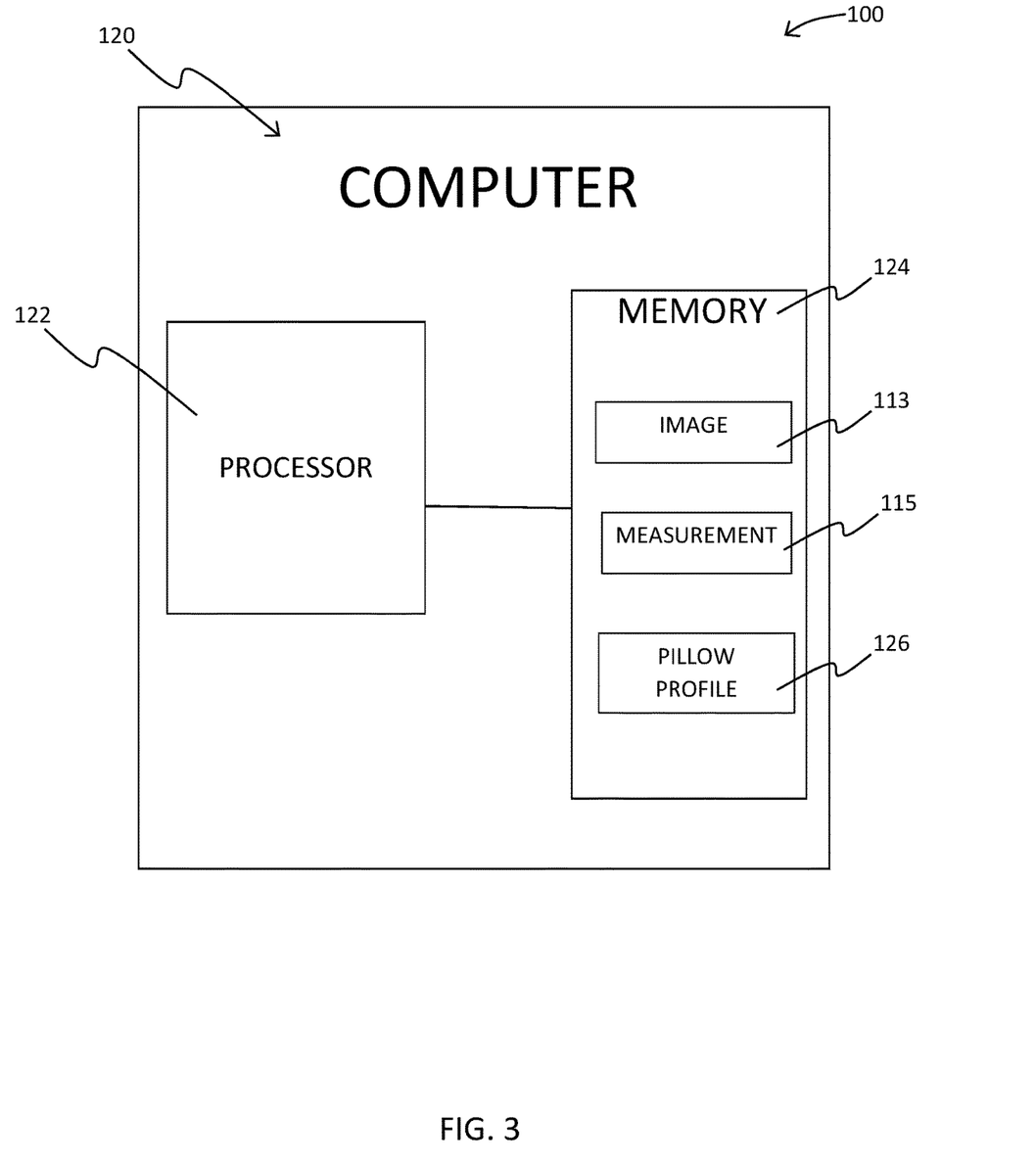
FIG. 3 is a front perspective view of the system of FIG. 1, according to an embodiment of the present disclosure.

FIG. 3 shows a front perspective view of the system 100 of FIG. 1, according to an embodiment of the present disclosure. The computer-device 120 may be communicably-coupled to the scanner-device 110. Further, the computer-device 120 may include a processor 122 and a memory 124. The processor 122 may be configured to receive the at least one image 113 of the at least one body-part 5 of the user 40 and the at least one measurement 115 of the at least one body-part 5 of the user 40 via the communication-means 116 (FIG. 2). Once received, the processor 122 may be configured to generate at least one pillow-profile 126 based on the at least one image 113 and the at least one measurement 115.

The memory 124 may be configured to store the at least one image 113, the at least one measurement 115 and the at least one pillow-profile 126. In one embodiment, the memory 124 may include a high-speed operating memory 124 such as random-access memory 124, and a storage memory 124 such as a database. The at least one image 113, the at least one measurement 115 and the at least one pillow-profile 126 may be stored in the database.

Figure 4:
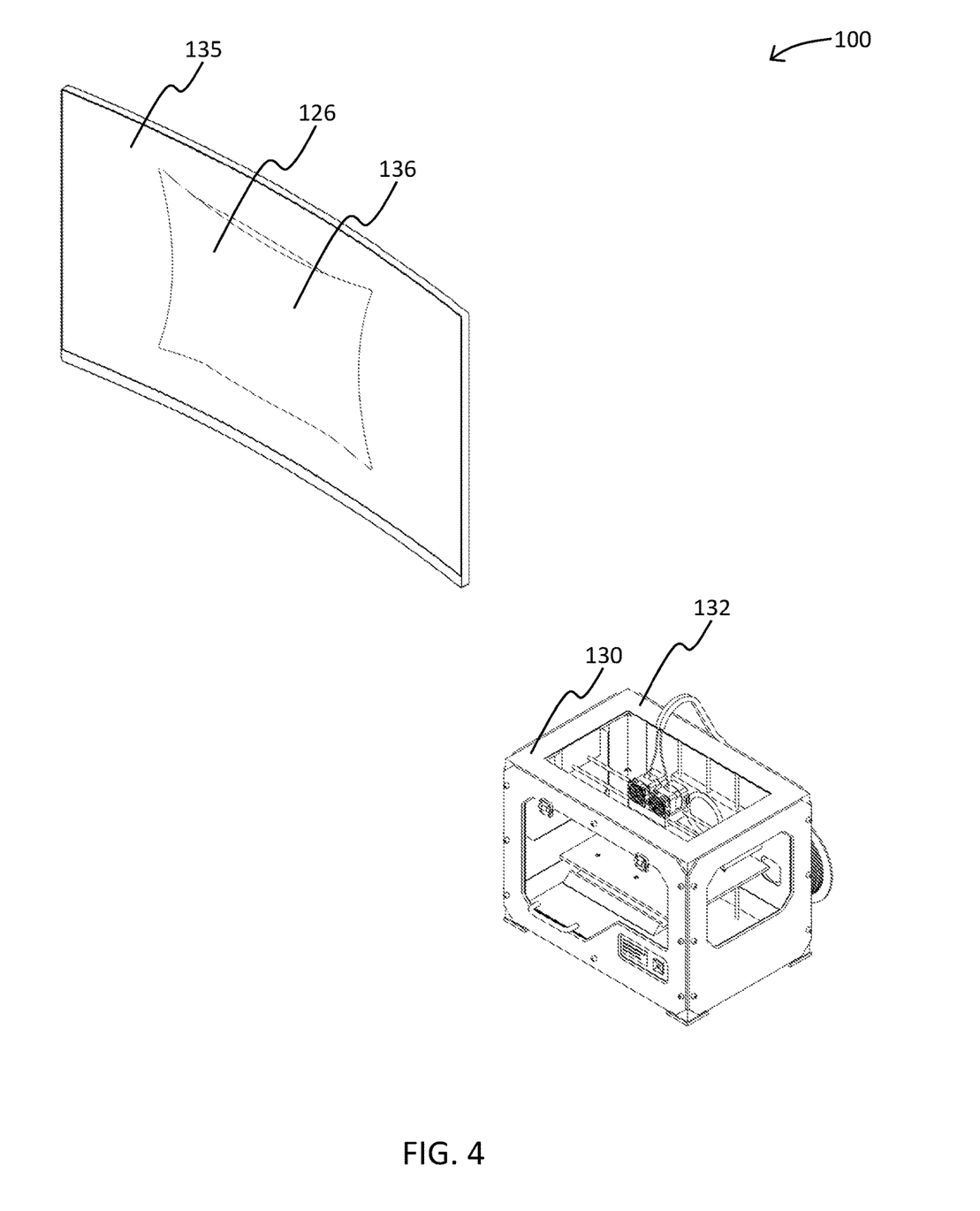
FIG. 4 is a front perspective view of the system of FIG. 1, according to an embodiment of the present disclosure.

Referring now to FIG. 4 showing a front perspective view of the system 100 of FIG. 1, according to an embodiment of the present disclosure. As shown, in one embodiment, the at least one pillow-profile 126 may be a three-dimensional model 136. Further, in this embodiment, the system 100 may further include a display-screen 135 configured to display the three-dimensional model 136. In this embodiment, the operator and user 40 may be able to view the three-dimensional model 136 prior to creation of the custom-pillow.

In addition, as shown, the system 100 may further include a reproduction-means 130 communicably-coupled to the computer-device 120. In this embodiment, the processor 122 may be configured to send the at least one pillow-profile 126 to the reproduction-means 130, such that the custom-pillow can then be created. In one embodiment, the reproduction-means 130 may be a three-dimensional printer 132 configured to produce a physical model of the custom-pillow. In other embodiments, the reproduction-means 130 may include a two-dimensional reproduction of the at least one pillow-profile 126 such that the custom-pillow can be made. The at least one pillow-profile 126 may include dimensions based off the at least one image 113 and the at least one measurement 115 (FIG. 3).

Figure 5:
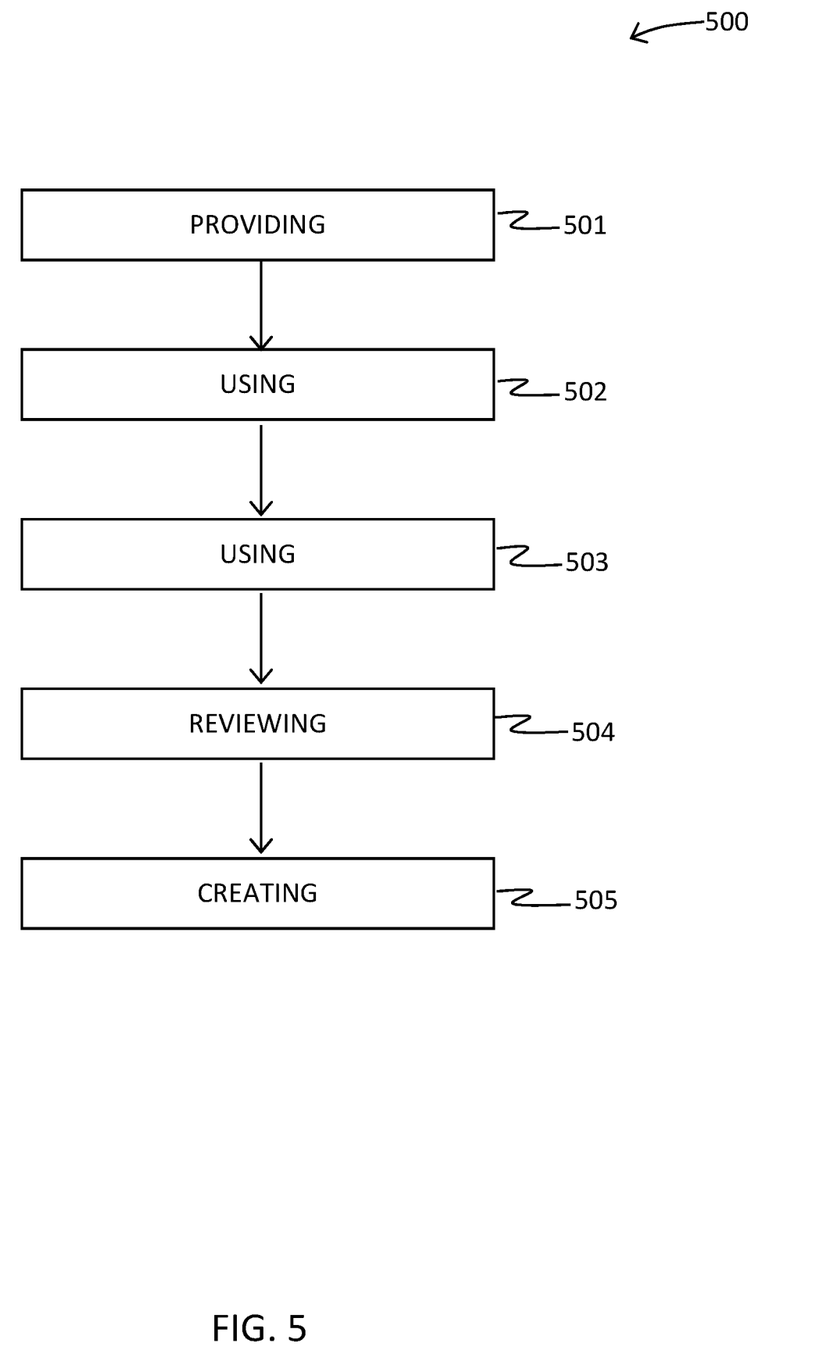
FIG. 5 is a flow diagram illustrating a method of use for system, according to an embodiment of the present disclosure.

FIG. 5 is a flow diagram illustrating a method of using a system for providing a custom-pillow 500, according to an embodiment of the present disclosure. As illustrated, the method of using a system for providing a custom-pillow 500 may include the steps of: step 501, providing the system 100 as above; step two 502, using the image-capture means 112 to capture the at least one image 113 of the at least one body-part 5 of the user 40; step three 503, using the measurement-means 114 to provide the at least one measurement 115 of the at least one body-part 5 of the user 40; step four 504, reviewing the at least one pillow-profile 126 of the user 40 based on the at least one image 113 and the at least one measurement 115; and step five 505, creating the custom-pillow based on the pillow-profile 126. In this method, the at least one body-part 5 of the user 40 may include the neck of the user 40 and the three images may include the supine-position of the neck, the right-side position of the neck, and the left-side position of the neck. Further, the at least one body-part 5 of the user 40 may include the head and the shoulder of the user 40. The at least one-measurement 115 may include a circumference-measurement of the head and the neck and the at least one-measurement 115 may further include a length-measurement from the shoulder to the head.

Figure 6:
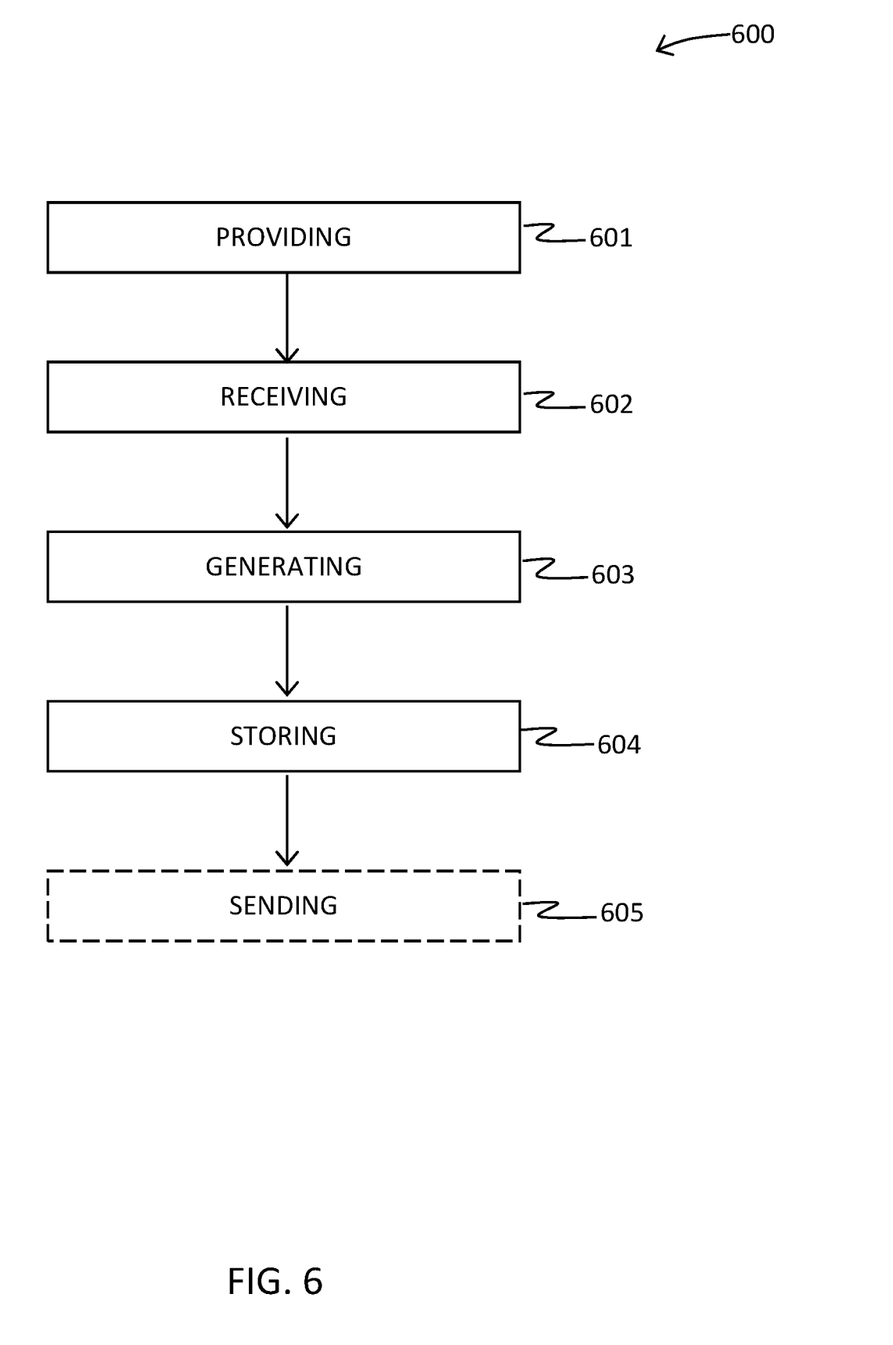
FIG. 6 is a flow diagram illustrating a method of use for system, according to an embodiment of the present disclosure.

FIG. 6 is a flow diagram illustrating method of providing a system for creating a custom-pillow 600, according to an embodiment of the present disclosure. As illustrated, the method of using a system for providing a custom-pillow 600 may include the steps of: step one 601, providing the system 100 as above; step two 602, receiving the at least one image 113 of the at least one body-part 5 of the user 40, and the at least one measurement 115 of the at least one body-part 5 of the user 40 at the processor 122; step three 603, generating the at least one pillow-profile 126 based on the at least one image 113 and the at least one measurement 115; step four 604, storing the at least one image 113, the at least one measurement 115 and the at least one pillow-profile 126 on the memory 124. Further steps may include: step five 605, sending the at least one pillow-profile 126 to a reproduction-means 130 for creating the custom-pillow.

It should be noted that step five 605 is an optional step and may not be implemented in all cases. Optional steps of method of providing 600 are illustrated using dotted lines in FIG. 6 so as to distinguish them from the other steps of method of providing 600. It should also be noted that the steps described in the method of use can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods for using system 100 (e.g., different step orders within above-mentioned list, elimination or addition of certain steps, including or excluding certain maintenance steps, etc.), are taught herein.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

Those with ordinary skill in the art will now appreciate that upon reading this specification and by their understanding the art of orthotics as described herein, methods of body-part analysis and evaluation for creating the custom orthotic pillow will be understood by those knowledgeable in such art.

What is claimed is new and desired to be protected by Letters Patent is set forth in the appended claims:

1. A system for providing a custom-pillow, the system comprising:
    a scanner-device including an image-capture means, a measurement-means and a communication-means, the image-capture means being configured to capture at least one image of at least one body-part of a user, and wherein the measurement-means is configured to provide at least one measurement of the at least one body-part of the user; and
    a computer-device communicably-coupled to the scanner-device, the computer-device including a processor and a memory, the processor being configured to receive the at least one image of the at least one body-part of the user and the at least one measurement of the at least one body-part of the user via the communication-means, and further configured to generate at least one pillow-profile based on the at least one image and the at least one measurement, and wherein the memory is configured to store the at least one image, the at least one measurement and the at least one pillow-profile;
    wherein the at least one image includes three images;
    wherein the at least one body-part of the user includes a neck;
    wherein the three images include a supine-position of the neck, a right-side position of the neck, and a left-side position of the neck.

2. The system of claim 1, wherein the at least one body-part of the user includes a head.

3. The system of claim 1, wherein the at least one body-part of the user further includes a shoulder.

4. The system of claim 1, wherein the at least one-measurement includes a circumference-measurement of the head and the neck.

5. The system of claim 1, wherein the at least one-measurement further includes a length-measurement from the shoulder to the head.

6. The system of claim 1, wherein the pillow-profile is a three-dimensional model.

7. The system of claim 6, further comprising a display-screen configured to display the three-dimensional model.

8. The system of claim 1, further comprising a reproduction-means communicably-coupled to the computing-device.

9. The system of claim 8, wherein the processor is configured to send the at least one pillow-profile to the reproduction-means.

10. The system of claim 9, wherein the reproduction-means is a three-dimensional printer.

11. The system of claim 1, wherein the image-capture means includes at least one imaging laser-beam.

12. The system of claim 1, wherein the measurement-means includes at least one measurement laser-beam.

13. A method of using a system for providing a custom-pillow, the method comprising the steps of:
    providing the system for providing the custom-pillow, the system including:
        a scanner-device including an image-capture means, a measurement-means and a communication-means, the image-capture means being configured to capture at least one image of at least one body-part of a user, and wherein the measurement-means is configured to provide at least one measurement of the at least one body-part of the user; and a computer-device communicably-coupled to the scanner-device, the computer-device including a processor and a memory, the processor being configured to receive the at least one image of the at least one body-part of the user and the at least one measurement of the at least one body-part of the user via the communication-means, and further configured to generate at least one pillow-profile based on the at least one image and the at least one measurement, and wherein the memory is configured to store the at least one image, the at least one measurement and the at least one pillow-profile; and using the image-capture means to capture the at least one image of the at least one body-part of the user;

using the measurement-means to provide the at least one measurement of the at least one body-part of the user;

reviewing the at least one pillow-profile of the user based on the at least one image and the at least one measurement;

creating the custom-pillow based on the pillow-profile;

wherein the at least one image includes three images;

wherein the at least one body-part of the user includes a neck; and wherein the three images include a supine-position of the neck, a right-side position of the neck, and a left-side position of the neck.

14. The method of claim 13, wherein the at least one body-part of the user further includes a head and a shoulder of the user; and wherein the at least one-measurement includes a circumference-measurement of the head and the neck; and wherein the at least one-measurement further includes a length-measurement from the shoulder to the head.

* * * * *